United States Patent [19]

Hsu et al.

[11] 4,318,860
[45] Mar. 9, 1982

[54] PREPARATION OF UNSATURATED MONESTER PRECURSOR FOR PELARGONIC ACID

[75] Inventors: Chao-Yang Hsu, Media; Haven S. Kesling, Jr., Drexel Hill, both of Pa.

[73] Assignee: Atlantic Richfield Company, Los Angeles, Calif.

[21] Appl. No.: 209,625

[22] Filed: Nov. 24, 1980

Related U.S. Application Data

[63] Continuation-in-part of Ser. No. 80,353, Sep. 28, 1979, abandoned.

[51] Int. Cl.³ .............................................. C07C 15/00
[52] U.S. Cl. ................................. 260/405.5; 260/409; 260/410.9 R
[58] Field of Search ......... 260/409, 410.9 R, 410.9 A, 260/410.9 M, 405.5; 560/209; 252/431 P, 431 C

[56] References Cited

U.S. PATENT DOCUMENTS

| | | | |
|---|---|---|---|
| 3,676,470 | 7/1972 | Takahashi | 260/410.9 A |
| 3,891,684 | 6/1975 | Jung | 252/431 P |
| 4,053,503 | 10/1977 | Burba | 260/407 |

*Primary Examiner*—John F. Niebling
*Attorney, Agent, or Firm*—Delbert E. McCaslin

[57] ABSTRACT

A process for producing unsaturated methyl nonadienoate and methyl nonatrienoate monesters useful as precursors for pelargonic acid which comprises contacting, in a reaction inert medium, butadiene and methyl-2,4-pentadienoate in a molar ratio of 2:1 to 10:1 at a temperature of 40° to 120° C. under an inert atmosphere and in the presence of a catalytic amount of a homogeneous palladium (II) complex of the formula

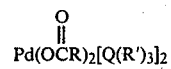

wherein R is alkyl, chloroalkyl, bromoalkyl or fluoroalkyl having from 1 to 6 carbon atoms or aryl having 6 to 12 carbon atoms; Q is phosphorous or arsenic and R' is alkyl, aminoalkyl or alkoxy having 1 to 6 carbon atoms or aryl or aryloxy having 6 to 12 carbon atoms.

The foregoing precursors may subsequently be hydrogenated to methyl pelargonate (methyl nonanoate) and pelargonic acid may then be obtained by acid-catalyzed hydrolysis of methyl pelargonate.

6 Claims, No Drawings

PREPARATION OF UNSATURATED MONESTER PRECURSOR FOR PELARGONIC ACID

CROSS REFERENCE TO RELATED APPLICATION

This application is a continuation-in-part of application Ser. No. 080,353, filed Sept. 28, 1979 abandoned.

BACKGROUND OF THE INVENTION

Various processes for the production of synthetic fatty acids are well known in the art. U.S. Pat. No. 2,384,817 describes the alkaline oxidation of an alcohol. This process requires a stoichiometric amount of alkali and hence a stoichiometric amount of acid.

British Pat. No. 849,951 discloses the oxidation of paraffin process which gives low quality fatty acids with poor color, odor and high peroxide and carbonyl content.

In the process which oxidizes an α-olefin as described in U.S. Pat. No. 3,692,810, a fatty acid of one less carbon atom than the starting material is obtained. Various types of by-products including carbon dioxide, formic acid, formaldehyde, other aldehydes, keto compounds, dibasic acids and polymers are also produced.

In the carboxylation of α-olefins as described in U.S. Pat. No. 3,819,669 considerable amounts of undesirable branched chain fatty acids are also produced.

Ziegler technology as described in U.S. Pat. No. 3,244,735 is used only for the production of even numbered carbon atom fatty acids and the yield of fatty acids is low.

Telomerization of ethylene described in U.S. Pat. No. 3,637,478 gives a wide range of odd number carbon atom fatty acids including $C_3$, $C_5$, $C_7$, $C_9$, $C_{11}$, and $C_{13}$ fatty acids.

At the present time there is no known prior art which describes the cross dimerization of 1,3-butadiene with methyl-2,4-pentadienoate to prepare the unsaturated linear dimers methyl nonadienoate and methyl nonatrienoate which may be hydrogenated to methyl pelargonate and hydrolyzed to pelargonic acid.

The Emery Process of ozonolysis of oleic acid results in the formation of a one-to-one ratio of azealaic and pelargonic acid.

The present invention is based on the discovery that methyl nonadienoate and methyl nonatrienoate monoesters can be prepared via a palladium (II)/tertiary phosphine complex catalyzed linear dimerization of methyl-2,4-pentadienoate with butadiene which monoesters may be converted by catalytic hydrogenation and subsequent hydrolysis to methyl pelargonate (methyl nonanoate) and pelargonic acid respectively.

BRIEF DESCRIPTION OF THE INVENTION

A process for producing a methyl nonadienoate and methyl nonatrienoate monoester useful as a precursor for pelargonic acid which comprises contacting, in a reaction inert medium, butadiene and methyl-2,4-pentadienoate in a molar ratio of 2:1 to 10:1 at a temperature of 40° to 120° C. under an inert atmosphere and in the presence of a catalytic amount of a homogeneous palladium (II) complex of the formula

wherein R is alkyl, chloroalkyl, bromoalkyl or fluoroalkyl having from 1 to 6 carbon atoms or aryl having 6 to 12 carbon atoms; Q is phosphorous or arsenic and R' is alkyl, aminoalkyl or alkoxy having 1 to 6 carbon atoms or aryl or aryloxy having 6 to 12 carbon atoms.

While the methyl nonadienoate is produced by the process of the invention in amounts of from about 5 to 15 mol percent, the major reaction product of the process is the methyl nonatrienoate unsaturated monoesters which may be for example schematically shown as follows:

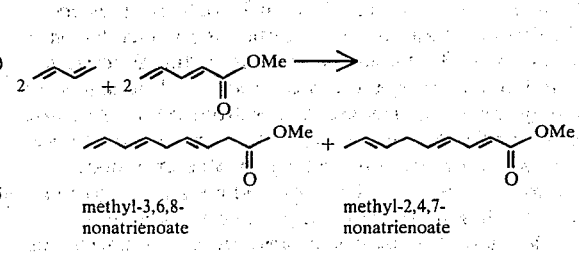

However, both monoesters are readily hydrogenated to methyl pelargonate.

DETAILED DESCRIPTION OF THE INVENTION

In accordance with the present invention, butadiene and methyl-2,4-pentadienoate are reacted in an autoclave or any other reactor suitable for obtaining an inert atmosphere in a molar ratio of 2:1 to 10:1 in the presence of a catalytic amount of a homogeneous palladium (II) complex of the formula

wherein R is alkyl, chloroalkyl, bromoalkyl or fluoroalkyl having from 1 to 6 carbon atoms or aryl having 6 to 12 carbon atoms; Q is phosphorous or arsenic and R' is alkyl aminoalkyl or alkoxy having 1 to 6 carbon atoms or aryl or aryloxy having 6 to 12 carbon atoms.

Generally, a catalytic amount of the homogeneous palladium (II) complex catalyst of the present invention ranges from about 0.1 to 5 mole percent of the starting methyl-2,4-pentadienoate. Preferably, the amount of catalyst is between 0.5 and 2 mole percent of said starting material.

The palladium (II) complex catalyst of the present invention is a homogeneous catalyst, i.e., it is soluble in the employed solvent medium. Typical examples of suitable solvents for the reaction inert medium of the present invention in which the catalyst is soluble include tetrahydrofuran (THF), benzene, toluene, methyl acetate, ethyl acetate, dioxane, acetonitrile, chloroform, dichloromethane and the like. Toluene and tetrahydrofuran (THF) are the preferred solvents. The catalyst may be preformed or generated in situ. In the latter case, the molar ratio of

to Q(R')₃ preferably ranges from 1:0.5 to 1:3.

Preferred inert atmospheres for the purpose of the present invention include nitrogen and carbon dioxide at a pressure range of 15 to 750 psig.

The reaction of butadiene and methyl 2,4-pentadienoate according to this invention should be conducted at a temperature of from 40° to 120° C. The preferred temperature is from 50° to 110° C. and the more preferred range from 80° to 100° C. The reaction time is generally from about 2 to 3 hours but may vary depending on temperature and catalyst concentration.

A high selectivity to the unsaturated methyl nonadienoate and methyl nonatrienoate monoesters of the process of the present invention is obtained by using an excess of 1,3-butadiene reactant in the dimerization reaction, and thus, the molar ratio of 1,3-butadiene to methyl-2,4-pentadienoate ranges from 2:1 to 10:1 and more preferably at a ratio of from about 4:1 to 8:1. Below a 2:1 molar ratio a large undesirable amount of methyl 2,4-pentadienoate homodimerization product will result and thus affect the process economics.

The methyl nonadienoate and methyl nonatrienoate containing reaction mixture of the present invention is preferably cooled to 0° C. to isolate the solid catalyst or the mixture can be subjected to fractional distillation so as to isolate the dimerization products and to recover the catalyst as a residue for possible recycle.

Catalytic hydrogenation of the precursor of the present invention can be carried out at a pressure of 1 to 50 atmospheres, preferably at 1 to 10 atmospheres and at a temperature of from 30° to 200° C., preferably from 100° to 125° C. The types of hydrogenation catalysts which may be employed in this hydrogenation have been extensively described in the prior art and any known hydrogenation catalyst, or mixture of catalysts, useful for the conversion of unsaturated esters to saturated esters may be used. Catalysts and the preparation thereof as described in U.S. Pat. Nos. 2,094,611, 2,201,235, and 3,374,184 and British Pat. Nos. 575,380, 1,151,567 and 1,181,137 may be used. In general heterogeneous catalysts comprising finely divided platinum, palladium, rhodium, ruthenium, cobalt and nickel which may be supported may be employed. Platinum oxides and palladium oxides, Raney nickel, platinum group metals on alumina or carbon may also be employed. Hydrogenation catalysts containing copper either in elemental form or combined with oxygen, as well as other hydrogenating metal oxides employed in conjunction with copper, supported or unsupported, may be used. Homogeneous hydrogenation catalysts may also be used, for example, sodium carbonate tris(triphenylphosphine)rhodium chloride as described in British Pat. No. 1,181,137, hydrido tris(triphenylphosphine) ruthenium (II) chloride, tris(triphenylphosphine)ruthenium chloride and tripyridine rhodium (III) chloride.

Methyl pelargonate, the product of the aforesaid hydrogenation, may be converted to pelargonic acid by conventional acid-catalyzed hydrolysis.

The following examples are for the purpose of illustrating the present invention and are not limiting to the scope thereof which is set forth in the claims.

EXAMPLE 1

Methyl-2,4-pentadienoate (50 mmole), palladium acetate (1.0 mmole), triphenylphosphine (2.0 mmole), and tetrahydrofuran (40 ml) were charged into an autoclave. After the autoclave was sealed and purged three times with nitrogen, 1,3-butadiene (189.3 mmole) was charged. Nitrogen (50 psig) was then introduced into the reaction system. While stirring, the reaction mixture was heated to 80° C. for 3 hours. After the reaction, the reaction mixture was cooled to room temperature, and the gas phase materials were vented and the catalyst was separated. The liquid reaction products were collected in a Parr hydrogenation bottle, and the contents were then subjected to hydrogenation in the presence of 5 percent palladium on carbon catalyst under 50 psig of hydrogen pressure. Analysis of the hydrogenated product by gas chromatography showed 53 percent selectivity to methyl pelargonate, resulting from the methyl nonadienoate and methyl nonatrienoate produced by the process, at 81 percent methyl-2,4-pentadienoate conversion. Other by-products included dimethyl sebacate (14 percent), and a cyclic dimer (12 percent) resulting from Diel-Alder reaction of methyl-2,4-pentadienoate.

EXAMPLES 2–3

Additional reactions were conducted employing the same experimental procedure as described in Example 1 with variations in reaction conditions. The results are shown in Table 1.

TABLE 1

| Example No. | 2 | 3 |
| --- | --- | --- |
| Reactant (mmole) catalyst | Pd(OAC)₂ (1.0) | Pd(OAC)₂(Pφ-3)₂ (1.0) |
| | Pφ₃ (2.0) | |
| MPD$^{(a)}$ | 50 | 50 |
| BD$^{(b)}$ | 83.7 | 200 |
| Toluene (ml) | 40 | 40 |
| Reaction Temperature (°C.) | 80 | 95 |
| Reaction Time (min.) | 120 | 180 |
| Conversion (mole %)$^{(c)}$ | 56 | 90 |
| Selectivity (mole %)$^{(d)}$ | | |
| Methyl pelargonate | 48 | 78 |
| Dimethyl sebacate | 40 | 15 |

$^{(a)}$MPD = Methyl-2,4-pentadienoate
$^{(b)}$BD = 1,3-butadiene
$^{(c)}$Calculated based on methyl-2,4-pentadienoate (mole %)
$^{(d)}$Calculated based on converted methyl-2,4-pentadienoate to the unsaturated monoesters giving methyl pelargonate on hydrogenation (mole %).

EXAMPLES 4–10

In Examples 4 to 10, which follow in Table 2 below the general procedure of Example 1 was repeated using various ratios of reactants and reaction conditions. The criticality of the butadiene to methyl-2,4-pentadienoate to give a high selectivity to the unsaturated methyl nonadienoate and methyl nonatrienoate and thus methyl pelargonate on hydrogenation is clearly demonstrated.

TABLE 2

| Example No. | 4 | 5 | 6 | 7 | 8 | 9 | 10 |
| --- | --- | --- | --- | --- | --- | --- | --- |
| Reactant (mmoles) | | | | | | | |

TABLE 2-continued

| Example No. | 4 | 5 | 6 | 7 | 8 | 9 | 10 |
|---|---|---|---|---|---|---|---|
| Catalyst | B | B | B | B | B | A | A |
| MPD[a] | 50 | 50 | 50 | 50 | 50 | 50 | 50 |
| BD[b] | 150 | 200 | 200 | 300 | 400 | 400 | 400 |
| Solvent (ml) | Toluene/40 | Toluene/40 | THF/40 | Toluene/40 | Toluene/40 | Toluene/40 | THF/40 |
| Reaction Temp. (°C.) | 95 | 95 | 95 | 95 | 95 | 100 | 80 |
| Reaction Time (min.) | 180 | 180 | 180 | 180 | 180 | 180 | 180 |
| Conversion (mole %)[c] | 73 | 91 | 87 | 93 | 96 | 99 | 81 |
| Selectivity (mole %)[d]* | | | | | | | |
| Methyl Pelargonate | 68 | 75 | 77 | 82 | 85 | 86 | 87 |
| Dimethyl Sebacate | 24 | 18 | 17 | 15 | 12 | 13 | 12 |

\* ~1–6% of heavies and other non-selective products also formed.
Catalyst A = Pd(OAC)$_2$ (1 mmole)/Ph$_3$P (2 mmole).
Catalyst B = Pd(OAC)$_2$(PPh$_3$)$_2$ (1.0 mmole).
[a]MPD = Methyl-2,4-pentadienoate
[b]BD = 1,3-butadiene
[c]Calculated based on methyl-2,4-pentadienoate (mole %)
[d]Calculated based on converted methyl-2,4-pentadienoate to the unsaturated monoesters giving methyl pelargonate on hydrogenation (mole %).

We claim:

1. A process for producing unsaturated methyl nonadienoate and methyl nonatrienoate monoesters useful as precursors for pelargonic acid which comprises contacting, in a reaction inert medium, butadiene and methyl-2,4-pentadienoate in a molar ratio of 2:1 to 10:1 at a temperature of 40° to 120° C. under an inert atmosphere and in the presence of a catalytic amount of a homogeneous palladium (II) complex of the formula

wherein R is alkyl, chloroalkyl, bromoalkyl or fluoroalkyl having from 1 to 6 carbon atoms or aryl having 6 to 12 carbon atoms; Q is phosphorous or arsenic and R' is alkyl, aminoalkyl or alkoxy having 1 to 6 carbon atoms or aryl or aryloxy having 6 to 12 carbon atoms.

2. The process of claim 1 wherein said temperature is from 80° to 100° C.

3. The process of claim 1 wherein said inert atmosphere is nitrogen or carbon dioxide at a pressure of 15 to 750 psig.

4. The process of claim 1 wherein said catalyst is generated in situ by admixing

with Q(R')$_3$ in a molar ratio of 0.5:1 to 1.5:1.

5. A process according to claim 1 wherein the butadiene to methyl-2,4-pentadienoate is employed at a molar ratio of from about 4:1 to 8:1.

6. The process of claim 1 wherein a solvent selected from the group consisting of tetrahydrofuran, benzene, toluene, methyl acetate, ethyl acetate, dioxane, acetonitrile, chloroform, and dichloromethane is employed as the reaction inert medium.

* * * * *